United States Patent [19]

Montgomery

[11] 4,210,745

[45] Jul. 1, 1980

[54] PROCEDURE FOR THE PREPARATION OF 9-β-D-ARABINOFURANOSYL-2-FLUOROADENINE

[75] Inventor: John A. Montgomery, Birmingham, Ala.

[73] Assignee: The United States of America as represented by the Department of Health, Education & Welfare, Washington, D.C.

[21] Appl. No.: 962,107

[22] Filed: Nov. 20, 1978

Related U.S. Application Data

[63] Continuation-in-part of Ser. No. 885,340, Mar. 10, 1978, abandoned, which is a continuation-in-part of Ser. No. 866,907, Jan. 4, 1978.

[51] Int. Cl.$^2$ .................... C07H 19/16; C07H 17/00
[52] U.S. Cl. ......................... 536/26; 536/24; 424/180
[58] Field of Search .................. 536/26, 24

[56] References Cited

U.S. PATENT DOCUMENTS 3,956,277   5/1976   Elion et al. ............... 536/26

FOREIGN PATENT DOCUMENTS 1338905  11/1973  United Kingdom ............ 536/26

OTHER PUBLICATIONS

Montgomery, J., and Hewson, K., J. Med. Chem., 12:498, (1969).
Keller, F., et al., J. Org. Chem., 32:1644, (1967).
Robins et al., J. Am. Chem. Soc., 75:263, (1953).
Brookman, et al., Biochem. Pharmacol., 26:2193, (1977).

Primary Examiner—Johnnie R. Brown
Assistant Examiner—Blondel Hazel
Attorney, Agent, or Firm—Jr., John S. Roberts

[57] ABSTRACT

The present invention is an improved multi-step process for the production of 9-β-D-arabinofuranosyl-2-fluoroadenine (2-F-AraA) and an improvement over the process of Montgomery and Hewson, J. Med. Chem., 12:498 (1969). This compound is an important tool in antitumor therapy and has shown activity against leukemia L1210 and P388 in animals as well as being a potent antiviral agent. Its therapeutic effectiveness occurs because 2-F-AraA is not a substrate for adenosine deaminase which vitiated against the activity of the parent compound 9-β-D-arabinofuranosyladenine (araA) as indicated in experimental animal cancers.

An advantage of making 2-F-AraA by the present process is that there is a sharply increased yield based on the chlorosugar up to about 400 percent. In the present improved process the differences lie in utilizing as a reactant 2,4,5,6-tetraaminopyrimidine; the acetylation of 2-aminoadenine in acetic acid and pyridine; the reaction of 2,6-diacetamidopurine with chlorosugar in ethylene chloride in the presence of a molecular sieve and subsequent deacetylation with methanolic sodium methoxide. Further, the diazotization step is carried out in a homogenous mixture of tetrahydrofuran and fluoboric acids. Finally, the O-benzyl groups are removed by the use of boron trichloride in ether.

5 Claims, No Drawings

PROCEDURE FOR THE PREPARATION OF 9-β-D-ARABINOFURANOSYL-2-FLUOROADENINE

This is a continuation-in-part of pending U.S. Ser. No. 885,340 filed Mar. 10, 1978, now abandoned, which is a continuation-in-part of pending U.S. Ser. No. 866,907 filed Jan. 4, 1978.

The invention described herein was made in the course of work under a grant or award from the Department of Health, Education, and Welfare.

The present invention is an improved procedure for the preparation of 9-β-D-arabinofuranosyl-2-fluoroadenine (2-F-AraA) utilizing as a reactant 2,4,5,6-tetraaminopyrimidine in which the overall yield based on the chlorosugar is increased markedly over the prior art.

The present improved process may be viewed in graphic form in the following chart:

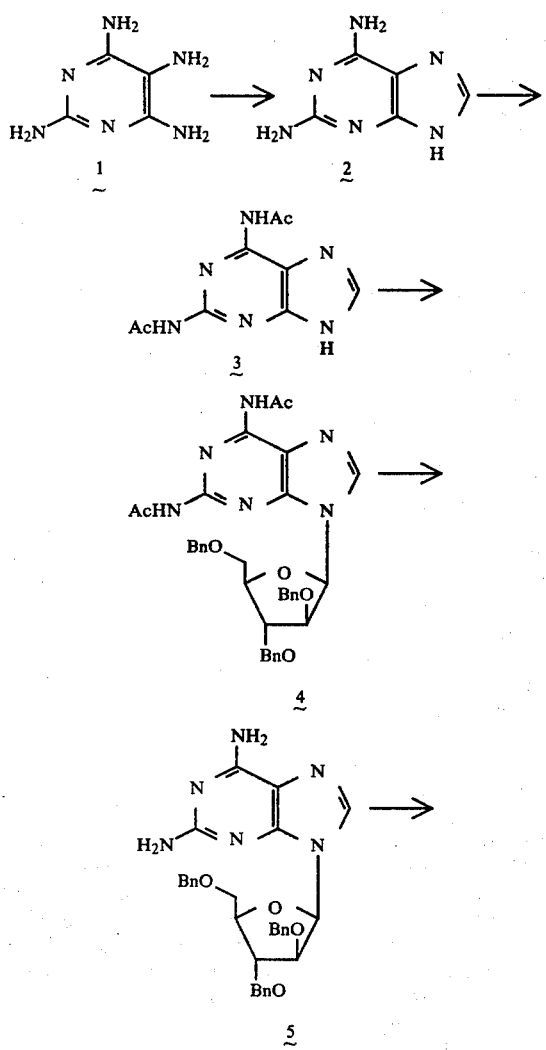

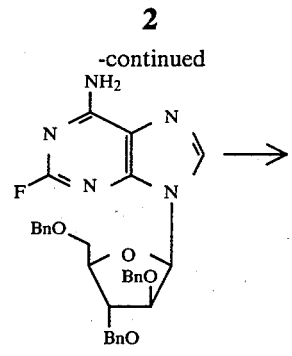

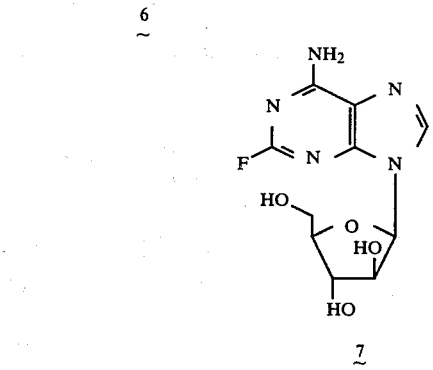

PRIOR ART STATEMENT

British Pat. No. 1,338,905 (1973) Wellcome Foundation, Inc. Portions of the process are generally described, as at page 3, column 2, lines 56–60, as follows: "Acylation of 2,6-diaminopurine, preferably with acetic anhydride, followed by condensation with an arabinose sugar halide, having its hydroxyl groups blocked with removable blocking groups Z."

Montgomery and Hewson, J. Med. Chem., 12:498 (1969). Scheme 1 at page 498, the written description at pages 498–500, and the discussion at page 504 of compound 9-β-D-arabinofuranosyl-2-fluoroadenine (2-F-AraA) represent the basic disclosure from which the present improved process was developed.

Brockman, Schabel, and Montgomery, Biochem. Pharmacol., 26:2193-2196 (1977) relates to the biologic activity of 9-β-D-arabinofuranosyl-2-fluoroadenine, a metabolically stable analog of 9-β-D-arabinofuranosyladenine.

Keller et al, J. Org. Chem., 32:1644 (1967) relates to the synthesis of 9-β-D-arabinofuranosyl-2-chloroadenine.

Robins et al, J. Chem. Soc., 75:263 (1953) teaches the cyclization of 4,5-diaminopyrimidines.

The present improved process leading to production of the antitumor compound 2-F-AraA differs from the above art both by step technique and by increased yield. With respect to the basic procedure outlined in Montgomery and Hewson above, the present procedure uses 2,4,5,6-tetraaminopyrimidine instead of 2,6-dichloropurine; the acetylation of 2-aminoadenine was carried out with acetic acid in pyridine; the reaction of 2,6-diacetamidopurine with halosugar is mandatory with chlorosugar in ethylenic chloride and this reaction is carried out in the presence of a molecular sieve. Deacetylation is then carried out with methanolic sodium methoxide. Diazotization of 5→6 was carried out in a homogenous mixture of tetrahydrofuran and 48% fluoboric acid in which the nucleoside 5 is soluble. The O-benzyl groups of 6 are removed by the use of boron trichloride in ether.

As to yield, the present process has increased yield from 4.79% to 17.5% based on the starting chlorosugar as compared with Montgomery and Hewson, J. Med. Chem., 12:498 (1969) and the procedure of U.S. Ser. No. 866,907 of John A. Montgomery.

The generalized procedure depicted in the above-noted chart is found both incrementally and wholly in the examples which follow.

GENERAL EXPERIMENTAL

All evaporations were carried out in vacuo with a rotary evaporator. All solvents were dried over Linde 4A molecular sieve and samples were normally dried in vacuo over phosphorus pentoxide at room temperature (unless otherwise stated) for 16 hours. Analtech precoated (250 μm) silica gel G(F) plates developed in chloroform-methanol (ratio specified for each compound) were used for the tlc analyses; the spots were detected by irradiation with a Mineralight and by charring after spraying with saturated ammonium sulfate. Melting points were determined with a Mel-Temp apparatus and are uncorrected. The uv absorption spectra were determined in 0.1 N hydrochloric acid (pH 1), pH 7 phosphate buffer, and 0.1 N sodium hydroxide (pH 13) with a Cary 17 spectrophotometer; the maxima are reported in nm ($\epsilon \pm 10^{-3}$). The nmr spectra were determined with a Varian XL-100-15 spectrometer in deuteriodimethylsulfoxide with tetramethylsilane as an internal reference: chemical shifts ($\epsilon$ in ppm) quoted in the case of multiplets are measured from the approximate center. Mass spectral data were obtained with a Varian MAT 311A instrument equipped with a combination EI/FI/FD ion source. The hplc analyses were carried out with a Waters Associates ALC-242 chromatograph with an M-6000 pump and equipped with a μBondapak $C_{18}$ column (¼"×30 cm) using the solvent systems specified. Quantitation was achieved by integration of the peaks.

2,4,5,6-Tetraaminopyrimidine (1) and 2-Aminoadenine (2). A suspension of 2,4,5,6-tetraaminopyrimidine (1) was utilized to form 2-aminoadenine (2) by using 251 g, (1.05 mole) of (1) in formamide (2510 ml) and heating with stirring until the pyrimidine dissolved to give an orange solution, which was boiled for 40 minutes. As the solution cooled, a precipitate formed. Water (1255 ml) was added to this mixture and the whole refrigerated overnight. The light brown solid, 2,6-diaminopurine sulfate, was collected, washed with water, and dried in vacuo, yield 196 g (45%). This material was dissolved with heat in water (3540 ml) containing concentrated hydrochloric acid (98 ml) to give a yellow solution, which was poured with stirring into 196 ml concentrated ammonium hydroxide. The hot solution was treated with charcoal and then filtered through Celite. The filtrate, on refrigeration overnight, gave 2,6-diaminopurine as a solid which was collected, washed with water, and dried in vacuo; yield, 106 g (75%). The 2-aminoadenine (2) was prepared by the method of Robins et al, J. Am. Chem. Soc., 75:263 (1953), which involves cyclization of the imidazole ring of the purine nucleus; yield 372 g. (55%).

2,6-Diacetamidopurine (3). A solution of 2-aminoadenine (2, 83.6 g., 557 mmoles) in a mixture of pyridine (1250 ml.) and acetic anhydride (168 ml.) was refluxed for 3 hours. On cooling overnight, the solution deposited a solid which was collected by filtration and washed with pyridine, ethanol, and then ether before it was dried overnight. This material was stirred with 1000 ml. of saturated sodium bicarbonate for 35 minutes, then diluted with 1000 ml. of water and stirred for 10 minutes, collected by filtration, and washed with water until all the bicarbonate was removed. The solid was dried overnight over phosphorus pentoxide in vacuo at room temperature and then at 100°. The yield was 87 g. (67%); m.p. 293°-295° (darkens at 230°); tlc homogeneous (3:1, 9:1).

2-Amino-9-(2,3,5-tri-O-benzyl-β-D-arabinofuranosyl)adenine (5). Dry hydrogen chloride gas was bubbled into a solution of 2,3,5-tri-O-benzyl-1-O-p-nitrobenzoyl-D-arabinofuranose (121 g., 212 mmoles) in methylene chloride (1.33 l at −10° to 0° for 2.5 hours. The precipitated p-nitrobenzoic acid was removed by filtration and washed with methylene chloride. The methylene chloride solution was evaporated in vacuo. The residue, dissolved in 1 l. of ethylene chloride, was added to a mixture of 2,6-diacetamidopurine (50.0 g., 213 mmoles) and molecular sieve (Linde 4A, 630 g.) in 6 l. of ethylene chloride. This mixture was refluxed until all the chlorosugar was consumed (tlc) (5 days). The mixture was then stirred with Celite and filtered. The solid was washed with chloroform and the combined filtrates were evaporated to dryness in vacuo. The residue was dissolved in benzene and filtered (to remove unreacted 2,6-diacetamidopurine). The filtrate was again evaporated to dryness in vacuo, producing 2,6-diacetamido-9-(2,3,5-tri-O-benzyl-β-D-arabinofuranosyl)adenine (4). The residue dissolved in 700 ml. of 1 N methanolic sodium methoxide. After a 3-hour reflux period, the solution was chilled, neutralized with acetic acid, and refrigerated overnight. The solid that precipitated was removed by filtration, washed with methanol, and dried in vacuo; yield 47 g. (40%); m.p. 160°-163°; tlc homogeneous (19:1).

9-(2,3,5-Tri-O-benzyl-β-D-arabinofuranosyl)-2-fluoroadenine (6). To a solution of 9-(2,3,5-tri-O-benzyl-β-D-arabinofuranosyl)adenine (5, 15.0 g., 27.1 mmoles) in a mixture of 500 ml. tetrahydrofuran and 1 l. of 48% fluoboric acid at −10° in a 4-l. beaker equipped with a mechanical stirrer was added dropwise in 20 minutes a saturated aqueous solution of sodium nitrite (7.5 g., 108 mmoles). The addition of sodium nitrite was repeated three times after which none of the 2-aminoadenine remained (tlc). The fluorboric acid was neutralized to pH 6 with 505% sodium hydroxide keeping the temperature between −40° and 0°. The solution was extracted four times with chloroform (300 ml., 250 ml., and two 200-ml. portions). The chloroform extract was washed with saturated sodium chloride solution and then dried over magnesium sulfate before it was evaporated to dryness in vacuo. The residual oil was dissolved in a liter of ethanolic ammonia (saturated at 0°), and the solution was allowed to stand for 4 days at 4° before it was evaporated to dryness. The residue was recrystallized from ethanol; yield 5.5 g. Additional material was recovered from the filtrate by recrystallization and the final filtrate was evaporated to dryness, diluted with 50 ml. of 1 N hydrochloric acid, stirred on a steam bath for 30 minutes, cooled, and the aqueous portion decanted. A chloroform solution of the residue was washed with saturated sodium bicarbonate, then water, and dried over magnesium sulfate before evaporation in vacuo. The residue was recrystallized from ethanol; total yield of 6, 7.2 g. (48%); m.p. 155°-157°. This material was essentially homogeneous according to tlc (19:1) and hplc [2 aqueous pentanesulfonic acid (0.005 M):3 acetonitrile-3% acetic acid].

9-β-D-Arabinofuranosyl-2-fluoroadenine (7). Boron trichloride gas was bubbled in methylene chloride (610 ml.) at 0° in a 2-l., 3-necked flask equipped with a thermometer, magnetic stirrer, and addition funnel and the stirred solution then cooled to −72° (dry ice-acetone) before the dropwise addition (1 hour) of a cold solution of 9-(2,3,5-tri-O-benzyl-β-D-arabinofuranosyl)-2-fluoroadenine (6, 7.0 g., 12.5 mmoles) in methylene chloride (70 ml.). After a total reaction time of 2.75 hours, the cooling bath was removed and the solvent and gas removed in vacuo. The residue was dissolved in cold methylene chloride (40 ml.) and the solution evaporated to dryness (6 times) or until a solid white residue was obtained, before adding 450 ml. of cold 5% sodium bicarbonate followed by solid sodium bicarbonate to adjust the pH to 6-7. The mixture was diluted with ethanol, heated to boiling, treated with charcoal, filtered through Celite, and then allowed to stand at room temperature overnight. It was then chilled and the solid collected by filtration, washed with cold water and then ether, and dried in vacuo; yield 3.23 g. (91%); m.p. 259°-260°; homogeneous according to tlc (19:1) and hplc (23 water:2 acetonitrile); nmr: 3.7 (m, $H_{4'}$ and $2H_{5'}$), 4.15 (m, $H_{2'}$ and $H_{3'}$), 5.1 (t, 5'—OH), 5.55 and 5.65 (2d, 2'-13 OH and 3'—OH), 6.14 (d, $J'_{2'}$ 3 Hz, $H_{1'}$), 7.8 (broad s, $NH_2$), 8.2 (s, $H_8$); uv: pH 1–262 (13.2); pH 7, 13–261 (15.3).

In (5) and (6) above where O-benzyl is indicated in the formula, the standard appreviation is O-Bn.

I claim:

1. In an improved multi-step process of preparing 9-β-D-arabinofuranosyl-2-fluoroadenine by the reaction of

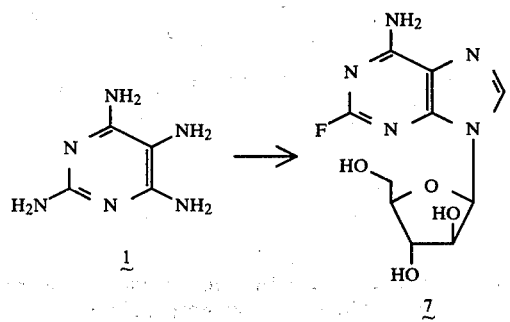

which includes

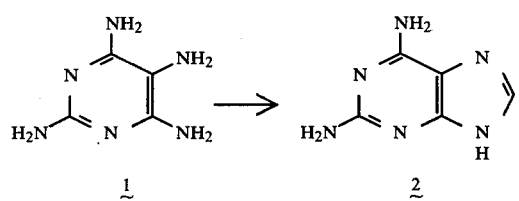

the improvement which utilizes

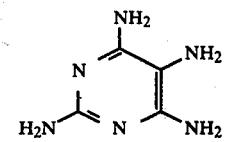

as a reactant and in the step

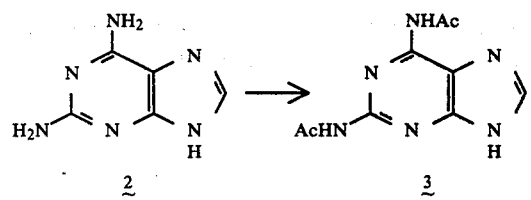

the improvement wherein the acetylation is carried out with acetic acid in pyridine and in the step

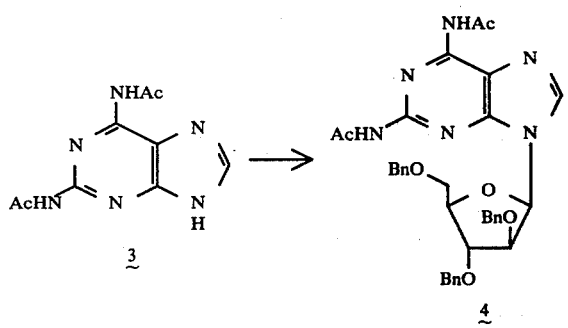

wherein a chlorosugar reactant is utilized in ethylene chloride in the presence of a molecular sieve and in the deacetylation step

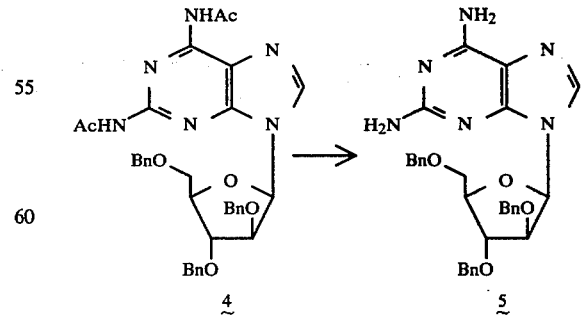

where deacetylation is carried out with methanolic sodium methoxide and in the step

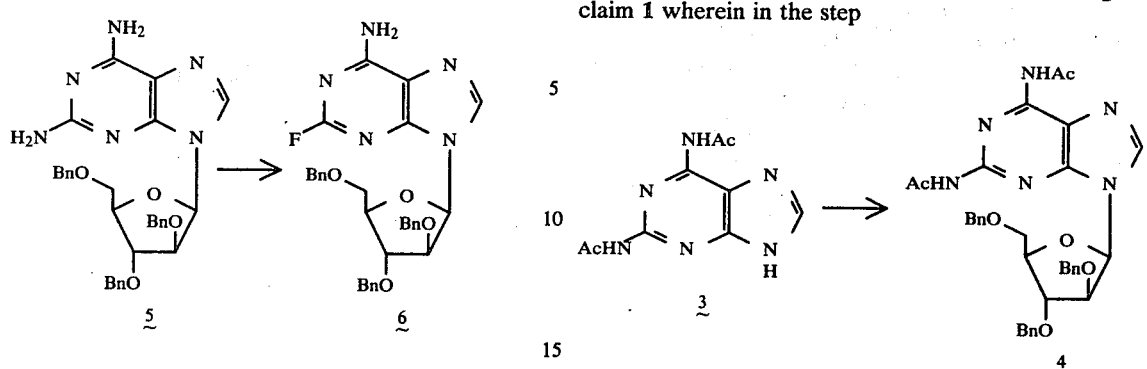

wherein the diazotization is carried out in a homogeneous mixture of tetrahydrofuran and fluorboric acid and in the step

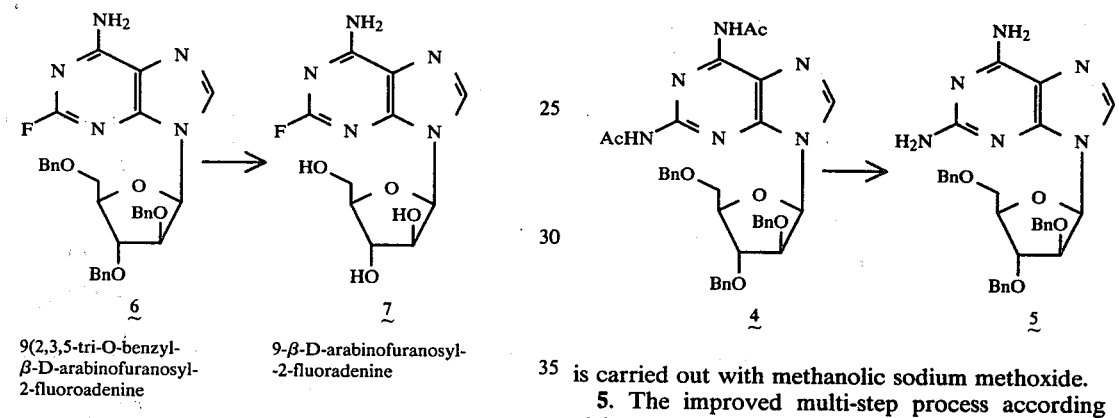

9(2,3,5-tri-O-benzyl-β-D-arabinofuranosyl-2-fluoroadenine

9-β-D-arabinofuranosyl-2-fluoradenine where the 2,3,5-tri-O-benzyl is converted to hydroxyl and the benzyl product groups are removed.

2. The improved multi-step process according to claim 1 wherein in the step

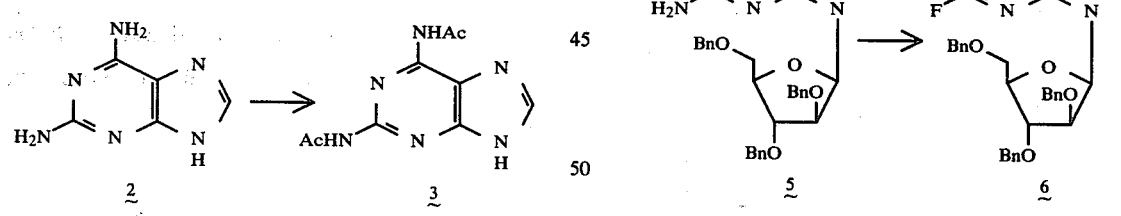

the acetylation is carried out with acetic acid in pyridine.

3. The improved multi-step process according to claim 1 wherein in the step a chlorosugar reactant is utilized in ethylene chloride.

4. The improved multi-step process according to claim 1 wherein the deacetylation step is carried out with methanolic sodium methoxide.

5. The improved multi-step process according to claim 1 wherein in the step the diazotization is carried out in a homogeneous mixture of tetrahydrofuran and fluoboric acid.

* * * * *